United States Patent
Liao et al.

(10) Patent No.: US 9,546,975 B2
(45) Date of Patent: Jan. 17, 2017

(54) EXAMINATION METHOD FOR DETECTING ABNORMAL ELECTROCHEMICAL TESTING STRIP

(71) Applicant: DELBio, INC., Taoyuan (TW)

(72) Inventors: Hung-Yun Liao, Taoyuan (TW); Chih-Wei Weng, Taoyuan (TW); Tsung-Hsuan Tsai, Taoyuan (TW); Miao-Ju Yen, Taoyuan (TW)

(73) Assignee: Delbio, Inc., Taoyuan (TW)

( * ) Notice: Subject to any disclaimer, the term of this patent is extended or adjusted under 35 U.S.C. 154(b) by 15 days.

(21) Appl. No.: 14/609,240

(22) Filed: Jan. 29, 2015

(65) Prior Publication Data

US 2016/0077038 A1    Mar. 17, 2016

(30) Foreign Application Priority Data

Sep. 12, 2014    (TW) .............................. 103131486 A (51) Int. Cl.
*G01N 27/327*    (2006.01)

(52) U.S. Cl.
CPC ................................ *G01N 27/3274* (2013.01)

(58) Field of Classification Search
CPC combination set(s) only.
See application file for complete search history.

(56) References Cited

U.S. PATENT DOCUMENTS

2007/0205114 A1* 9/2007 Mathur .............. G01N 27/3274
                                                        205/792
2012/0271559 A1  10/2012 Carpenter et al.

\* cited by examiner

*Primary Examiner* — Clayton E Laballe
*Assistant Examiner* — Jas Sanghera
(74) *Attorney, Agent, or Firm* — Muncy, Geissler, Olds & Lowe, P.C.

(57) ABSTRACT

An examination method for detecting abnormal electrochemical testing strip includes the steps of: applying a trigger voltage to a testing strip; injecting a target sample to the testing strip; obtaining a trigger current which is generated by injecting the target sample to the testing strip; comparing the trigger current with a first threshold, and determining whether the trigger current is lager than or equal to the first threshold; and when the trigger current is less than the first threshold, displaying a message for abnormality.

19 Claims, 9 Drawing Sheets

EXAMINATION METHOD FOR DETECTING ABNORMAL ELECTROCHEMICAL TESTING STRIP

CROSS REFERENCE TO RELATED APPLICATIONS

This Non-provisional application claims priority under 35 U.S.C. §119(a) on patent application No(s). 103131486 filed in Taiwan. Republic of China on Sep. 12, 2014, the entire contents of which are hereby incorporated by reference.

BACKGROUND OF THE INVENTION

Field of Invention

The invention relates to an examination method for detecting abnormal testing strip and, in particular, to an examination method for detecting abnormal electrochemical testing strip.

Related Art

Electrochemical analysis method is commonly used in the substance examination or concentration examination, and developed into a test-and-know sensor due to its rapid and convenient examination. Further, the above mentioned sensor is commonly formed into a testing strip nowadays. The electrochemical analysis method can be applied to many fields, such as environment, agriculture, medicine or biochemistry analysis. The electrochemical analysis method is a high-sensitivity (heavy) metal examination method and can detect even a low concentration. In medicine, the domestic blood-glucose meter is a really successful case for the electrochemical analysis method applied to the testing strip.

The testing strip described in this invention is designed according to the electrochemical analysis method, and can be called an electrochemical testing strip. In general, the testing strip has a space therein for holding a target sample, and includes two electrodes so that the target sample and the reagent on the electrode surface (or the reagent contacting a part of the electrodes) can generate the corresponding electrochemical action, and therefore a current value can be detected according to the concentration of the target sample. In other words, concentration of the target sample can be deduced from the current value. The target sample is variable according to the application field of the testing strip, or the blood sample used in the blood glucose detection.

However, trigger current of the conventional electrochemical testing strip and method required for the electrochemical reaction is not quite high enough in value, so the sensing procedure is easy to be promptly started after the switch is turned on. Hence, examination for the abnormal condition can not be effectively executed (unless the testing strip is fully damaged or has a gross flaw), and therefore the sensing data acquired may be generated from the abnormal electrochemical testing strip and that will also be an error data. In practical, the ex-factory electrochemical testing strip lacks of a mechanism or design capable of effectively detecting the abnormal condition, such as abnormal circuit resistance of the testing strip or unsuitable enzyme content of the reagent for specific sample or testing target. Therefore, the user can't sense the abnormal condition of the testing strip, and thus continuously uses the abnormal testing strip to acquire the abnormal reading which will cause an erroneous judgment. Especially, when the testing strip is applied to the medicine use, for example, the blood glucose testing, the abnormal reading may further hurt the user's health and safety due to error data.

Therefore, it is an important subject to provide an examination method for detecting abnormal electrochemical testing strip while the testing strip is used, and the abnormal testing strip can display abnormal data instead of directly reading so that the erroneous judgment of the user can be prevented.

SUMMARY OF THE INVENTION

In view of the foregoing subject, an objective of this invention is to provide an examination method for detecting abnormal electrochemical testing strip while the abnormal testing strip is used and can be displayed an abnormal data on examination device instead of reading, so that the erroneous judgment of the user can be prevented.

To achieve the above objective, an examination method for detecting abnormal electrochemical testing strip according to this invention includes the steps of: applying a trigger voltage to a testing strip; injecting a target sample to the testing strip; obtaining a trigger current which is generated by injecting the target sample to the testing strip; comparing the trigger current with a first threshold, and determining whether the trigger current is lager than or equal to the first threshold; and when the trigger current is less than the first threshold, displaying a message for abnormality.

In one embodiment, the examination step enters into a reaction stage when the trigger current is larger than or equal to the first threshold.

In one embodiment, the reaction stage indicates the stage when the target sample generates the electrochemical reaction, and a first driving voltage is supplied into the reaction stage to obtain a first reading current.

In one embodiment, the examination method further comprises steps of: supplying the first driving voltage to the testing strip and then resting the testing strip for a time interval to obtain a second reading current; comparing the ratio of the first reading current to the second reading current with a second threshold to determine whether the ratio is larger than or equal to the second threshold; and displaying the message for abnormality when the ratio is less than the second threshold.

In one embodiment, the examination method further comprises a step of: when the ratio is larger than or equal to the second threshold, supplying a second driving voltage to the testing strip to obtain a third reading current after the testing strip is rested for the time interval.

In one embodiment, the examination method further comprises a step of: calibrating a blood glucose reading of the target sample according to the third reading current.

In one embodiment, the time for the rest is between 1 second and 2 seconds.

In one embodiment, the second threshold is between 1.5 and 2.5 times.

In one embodiment, the first threshold is between 800 and 1200 nA.

In one embodiment, wherein before the step of comparing the trigger current with the first threshold, the examination method further comprises steps of: comparing the trigger current with a lowest threshold to determine whether the trigger current is larger than or equal to the lowest threshold; displaying a no-sample message when the trigger current is less than the lowest threshold, or entering into the step of comparing the trigger current with the first threshold when the trigger current is larger than or equal to the lowest threshold.

In one embodiment, the lowest threshold is less than the first threshold.

In one embodiment, the lowest threshold is between 300 and 600 nA.

To achieve the above objective, an examination method for detecting abnormal electrochemical testing strip according to this invention comprises steps of: applying a trigger voltage to a testing strip; injecting a target sample to the testing strip; obtaining a trigger current which is generated by injecting the target sample to the testing strip; comparing the trigger current with a first threshold, and determining whether the trigger current is lager than or equal to the first threshold; displaying a message for abnormality when the trigger current is less than the first threshold, or entering into a reaction stage when the trigger current is larger than or equal to the first threshold; supplying a first driving voltage to the testing strip in the reaction stage to obtain a first reading current; resting the testing strip for a time interval to obtain a second reading current; comparing the ratio of the first reading current to the second reading current with a second threshold to determine whether the ratio is larger than or equal to the second threshold; and displaying the message for abnormality when the ratio is less than the second threshold.

In one embodiment, wherein after the step of supplying the first driving voltage to the testing strip in the reaction stage, the examination method further comprises a step of: supplying a second driving voltage to the testing strip to obtain a third reading current when the ratio is larger than or equal to the second threshold.

In one embodiment, the examination method further comprises a step of: calibrating a blood glucose reading of the target sample according to the third reading current.

In one embodiment, the time for the rest is between 1 second and 2 seconds.

In one embodiment, the first threshold is between 800 and 1200 nA.

In one embodiment, the second threshold is between 1.5 and 2.5 times.

In one embodiment, wherein before the step of comparing the trigger current with the first threshold, the examination method further comprises steps of: comparing the trigger current with a lowest threshold to determine whether the trigger current is larger than or equal to the lowest threshold; display a no-sample message when the trigger current is less than the lowest threshold, or entering into the step of the comparison with the first threshold when the trigger current is larger than or equal to the lowest threshold.

In one embodiment, the lowest threshold is between 300 and 600 nA.

As mentioned above, in the examination method for detecting abnormal electrochemical testing strip of this invention, the dynamic balance existing between the trigger current and the reading current which are generated due to the electrochemical reaction of the target sample is used, and thereby the trigger current and a threshold (i.e. the above-mentioned first threshold) are compared with each other to determine whether the testing strip is abnormal or not. If it is determined that the trigger current is less than the first threshold, it represents the testing strip is probably abnormal so as to lead to a too small trigger current, and therefore a message for abnormality can be displayed on examination device or by other mechanism. Therefore, the message for abnormality is directly displayed to inform the user while the subsequent reaction stage (i.e. the stage where the target sample and the reagent together generate the electrochemical reaction) needn't be executed, so that displaying the abnormal (erroneous) reading and the misjudgment of the user can be avoided. It is noted that the terms "display", "displaying", or "displayed" described in this disclosure means that an action to inform user, and it is not to limit manners of informing, so that either by visually showing text or image, or making sounds or beeps, or vibrations . . . etc. are all in sense of the invention.

After examination step enters into the reaction stage, the first driving voltage is supplied to make the target sample provided in the testing strip and the reagent together generate the electrochemical reaction, and to measure the first reading current. Then, the testing strip is rested for a short time period or interval, and the second reading current is measured when the electrochemical reaction tends to become gentle. The ratio of the first reading current to the second reading current has a specific range during the dynamic balance method, and thereby it can be determined that whether the testing strip is at a normal reaction state. Accordingly, another threshold (i.e. the above-mentioned second threshold) is used to determine whether the testing strip is sufficiently worked, and therefore the corresponding reading can be obtained as a reasonable and reliable one.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

In this embodiment, the electrochemical testing strip is made by conforming to the principle of the electrochemical examination technology, and directly called the "testing strip" hereinafter for the convenient illustration. Furthermore, the testing strip of this embodiment can be applied to many fields, such as environment examination, food examination, or medical blood-glucose detection. For the convenient understanding, the following embodiments use the electrochemical testing strip applied to the blood-glucose detection as an example for the illustration.

Figure 1:
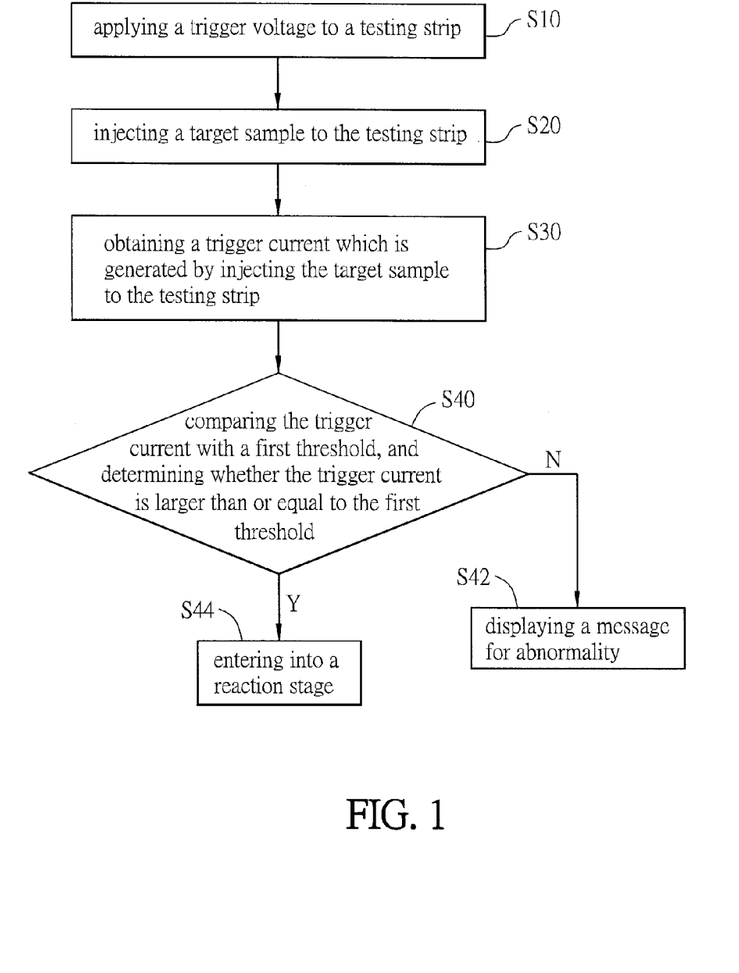
FIG. 1 is a schematic flowchart of an examination method for detecting abnormal electrochemical testing strip of an embodiment of the invention.

FIG. 1 is a schematic flowchart of an examination method for detecting abnormal electrochemical testing strip of an embodiment of the invention. In this embodiment, the above-mentioned electrochemical reaction based examination method is called "the method" for the convenient illustration. As shown in FIG. 1, the method includes at least the steps of: applying a trigger voltage to a testing strip (step S10); injecting a target sample to the testing strip (step S20); obtaining a trigger current (TC) which is produced by injecting the target sample to the testing strip (step S30); comparing the trigger current with a first threshold (TH1), and determining whether the trigger current TC is lager than or equal to the first threshold TH1 or not (step S40); when the trigger current TC is smaller or less than the first threshold TH1, displaying a message for abnormality (step S42) representing that the testing strip may be abnormal so as to be inapplicable, or when the trigger current TC is larger or more than or equal to the first threshold TH1, entering into a reaction stage RS (step S44).

Figure 2A:
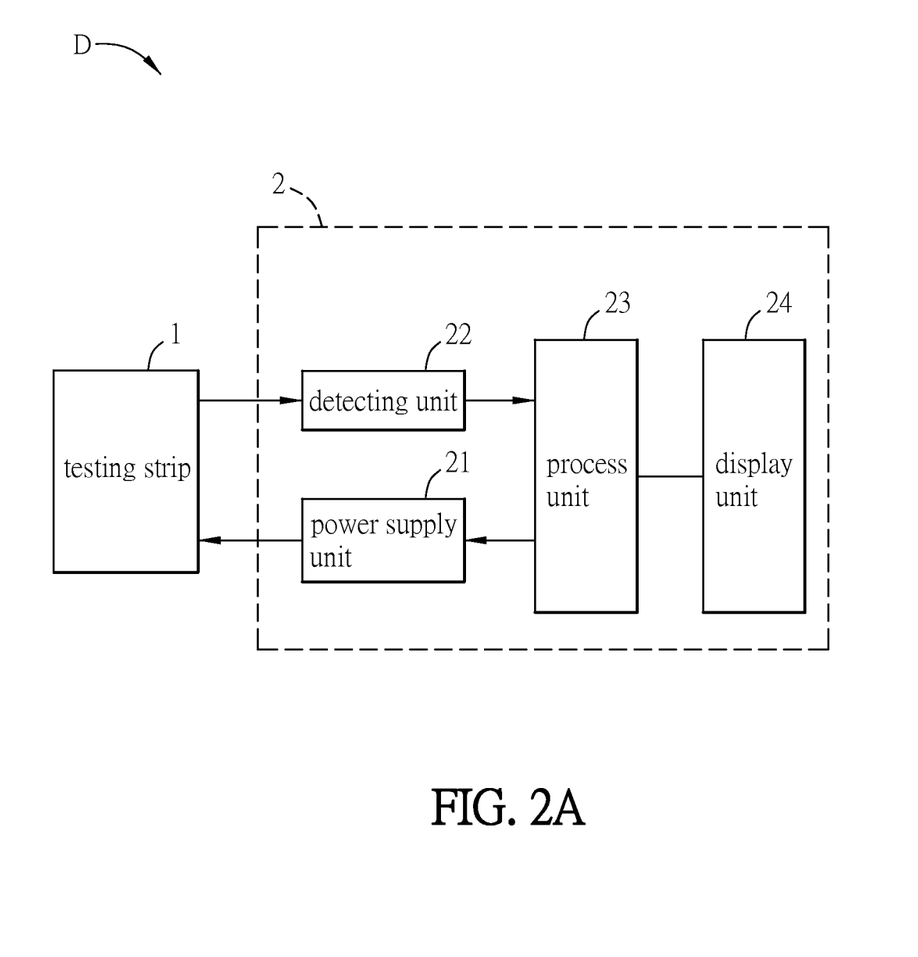
FIG. 2A is a schematic block diagram of the examination device applied to the examination method shown in FIG. 1.

For making the related details of the steps of this embodiment clearer, the following illustration will be given with an examination device D. FIG. 2A is a schematic block diagram of the examination device applied to the method shown in FIG. 1. As shown in FIGS. 1 and 2A, the examination device D of this embodiment includes at least a testing strip 1 and a measuring module 2. The measuring module 2 can execute the method shown in FIG. 1 to determine whether the testing strip 1 is abnormal or not. Besides, in the following embodiments, the target sample is the liquid whole blood sample for example. The structure and constitution of the examination device D will be illustrated first, and then how to execute the method on the examination device D will be illustrated accordingly. However, should be noted, the following embodiments are just for the illustrative purpose but not for limiting the scope of this invention.

As shown in FIG. 2A, the testing strip 1 is electrically connected to the measuring module 2. In physical, the examination device D can have a tank, slot, or space for containing at least part of the testing strip 1 therein. The size and shape of the tank is designed according to the form or shape of the testing strip 1, and the tank can be configured with a structure for the electrical connections, such as an I/O port, so that the testing strip 1 can be electrically connected with the measuring module 2 after disposed into the tank. The measuring module 2 further includes a power supply unit 21, which can supply power, or said voltage, to the testing strip 1 (as the step S10). In this embodiment, the testing strip 1 is supplied by the power supply unit 21 with a trigger voltage, and the trigger voltage is less than 1V favorably. The trigger voltage of this embodiment is 0.3V for example, but this invention is not limited thereto. Then, in the step S20, the user can inject a target sample to the testing strip 1, and the target sample of this embodiment is the blood sample of whole blood, as mentioned above.

Figure 2B:
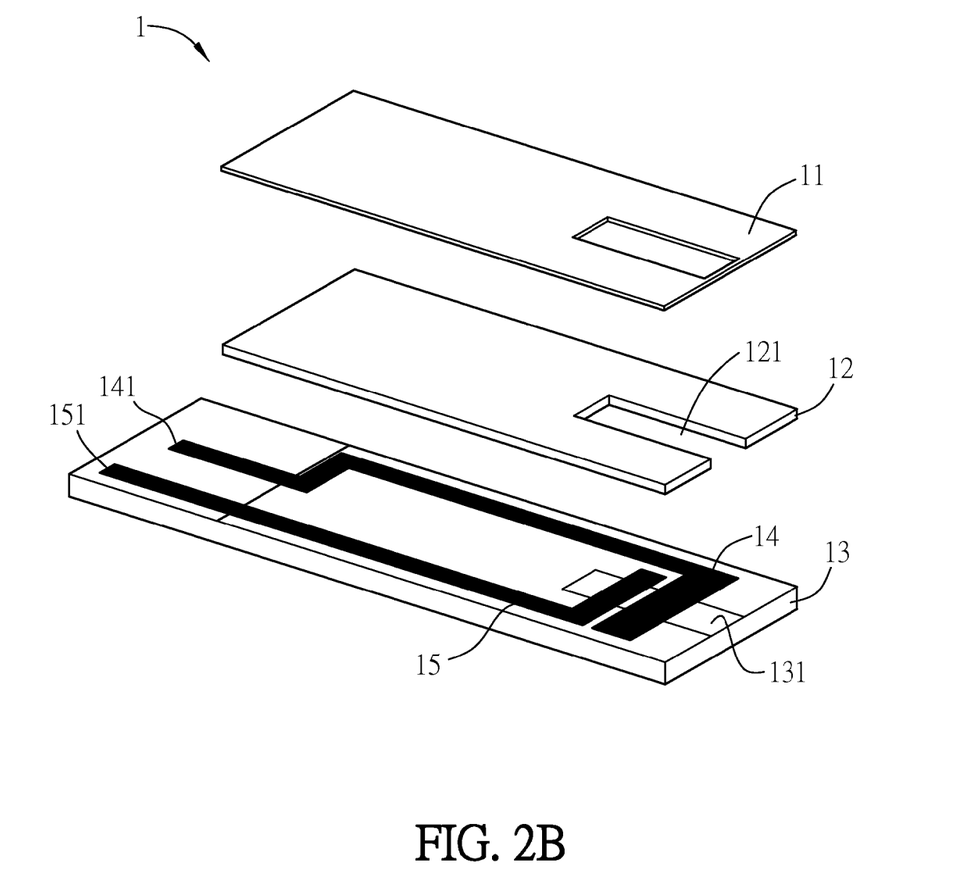
FIG. 2B is a schematic exploded diagram of the testing strip in FIG. 2A.

Furthermore, the testing strip 1 can include at least an upper cover layer 11, an intermediate layer 12, two electrodes and a substrate layer 13, as shown in FIG. 2B, which is a schematic exploded diagram of the testing strip in FIG. 2A. The substrate layer 13 is an electrical insulation substrate. The two electrodes in this embodiment are for example a working electrode 14 and an auxiliary electrode 15, and the mentioned electrode structure can be made to have a required pattern by the screen printing method and be printed on the substrate layer 13. Besides, the relative position, shape, and size of the working electrode 14 and auxiliary electrode 15 are not limited in this invention. One end substantially along a longitudinal direction of the substrate layer 13 has a cathode 141 and an anode 151, which are formed by the working electrode 14 and the auxiliary electrode 15 respectively and have no contact therebetween. Likewise, the relative relation of the cathode 141 and anode 151 is not limited here, which can be determined according to the relative relation of the electrochemical cell connection and electron flow. The other end substantially along the longitudinal direction of the substrate layer 13 has a reaction portion 131, and at least a part of each of the two electrodes 14 and 15 is disposed at and covers the reaction portion 131. In detail, the intermediate layer 12 is disposed on the substrate layer 13 and includes an injection portion (an opening) 121 corresponding to the reaction portion 131 in this embodiment. Since the intermediate layer 12 has a certain thickness, a space for accommodating the blood sample can be defined when the upper cover layer 11, the intermediate layer 12 and the substrate layer 13 are combined. Therefore, in the step S20, the user can inject the blood (target sample) to fill the reaction portion 131 through the injection portion 121 of the intermediate layer 12.

When the blood (target sample) enters through the injection portion 121 of the intermediate layer 12 and fills the reaction portion 131, at least parts of the working electrode 14 and the auxiliary electrode 15 can contact the target sample to result in the subsequent electrochemical reaction. Since the related electrochemical technique is comprehended by those skilled in the art, the related description is omitted here for conciseness.

However, the details of the electrochemical technique related to this embodiment are still mainly illustrated as below. A reagent is fixed to proper areas on the reaction portion 131 and can be made reaction with an under-test object in the target sample (just the blood glucose in the target sample in this embodiment) to generate an electrochemical reaction so as to generate an electrical output signal which can be measured, wherein the electrical output signal is a current value for example. The examination method of detecting abnormal testing strip of this embodiment is developed by using the electrical output signal generated due to the electrochemical effect. As shown in FIG. 2A, the measuring module 2 further includes a detecting unit 22, which can receive the electrical output signal and convert it into a current value. The current variation is shown in FIG. 3, which is a schematic diagram of the time-current variation measured by the measuring module in FIG. 2A.

Figure 3:
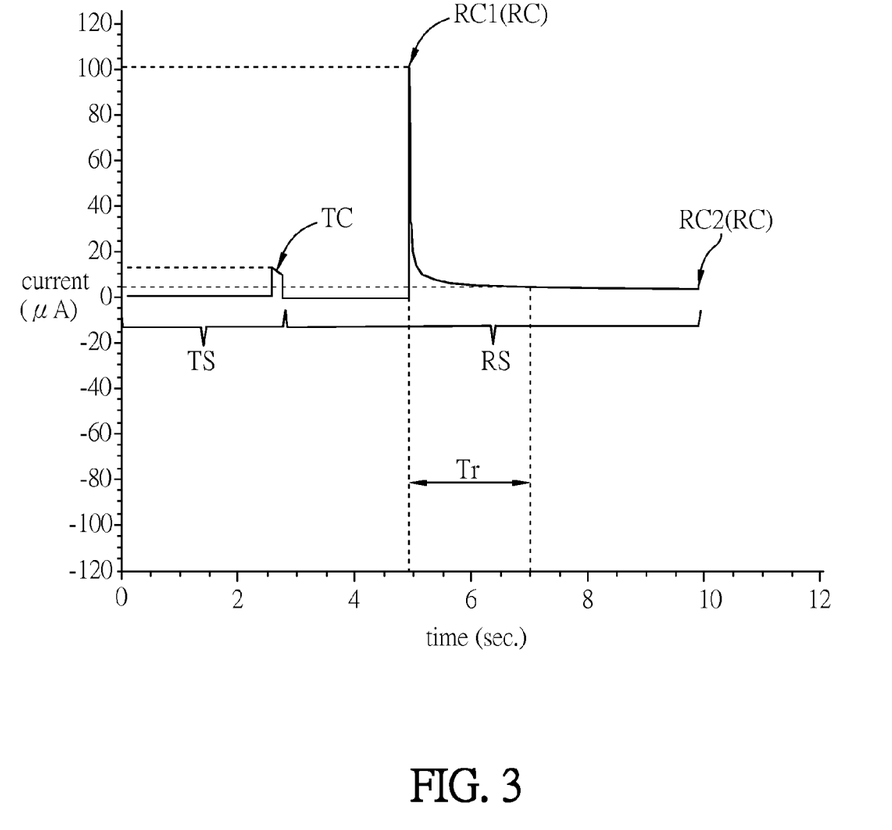
FIG. 3 is a schematic diagram of the time-current variation measured by the measuring module in FIG. 2A.
Figure 4A:
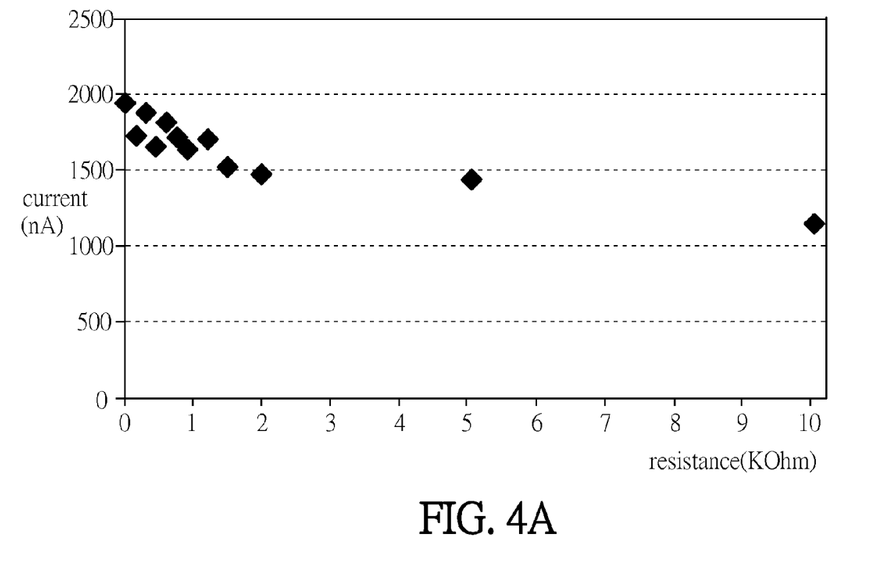
FIG. 4A is a schematic diagram of the trigger current measured by the measuring module in FIG. 2A.
Figure 4B:
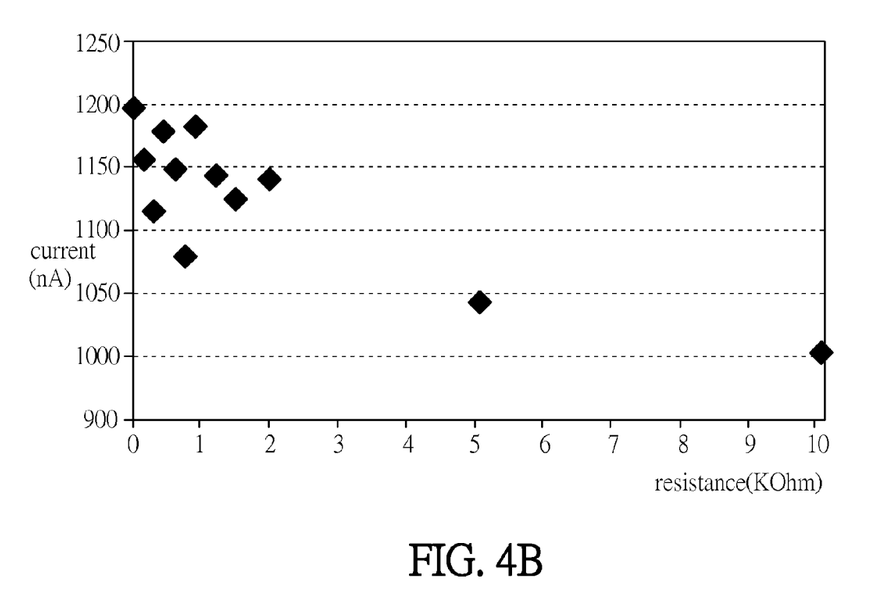
FIG. 4B is a schematic diagram of the reading current measured by the measuring module in FIG. 2A.

As shown in FIG. 3, after the target sample is injected into the testing strip 1, different electrical output signals can be generated during different stages. A trigger current TC is generated in the trigger stage, which is shown as a time period or interval marked as TS, and a reading current RC (which can be further divided into the first reading current RC1 and the second reading current RC2 in the following illustration) is generated in the reaction stage, which is shown as a time period or interval marked as RS. The trigger current TC and the reading current RC have a relationship of dynamic balance. The so-called "dynamic balance" here indicates the reading current RC will be abnormal when the trigger current TC is abnormal. Therefore, the method for detecting abnormal testing strip of this embodiment can be regarded as a kind of multi-thresholds debugging method developed by the dynamic balance theory or property of the trigger current TC and reading current RC. FIG. 4A is a schematic diagram of the trigger current measured by the measuring module in FIG. 2A, and FIG. 4B is a schematic diagram of the reading current measured by the measuring module in FIG. 2A. To be noted, the data of the trigger current TC and reading current RC shown in FIGS. 4A and 4B are derived from a known abnormal testing strip 1. As shown in FIGS. 4A and 4B, the X axis represents the resistance value of the testing strip 1 (the higher resistance represents the more abnormal situation, unit: K Ohm), and the Y axis represents the current value measured by the measuring module 2 (unit: nA). As shown in FIGS. 4A and 4B, with the ascending resistance, the trigger current TC and the reading current RC both have a descending tendency, and this characteristic is just the above-mentioned dynamic balance. To be noted, the test environment of FIGS. 4A and 4B is the blood sample of high HCT value, and the data are acquired from the sample with a low blood glucose concentration, such as the test environment with HCT value of 70, and blood glucose concentration of 20 mg/dL for example.

As shown in FIGS. 1 and 3, in this invention, the dynamic balance is applied, and the trigger current TC is compared with a defined threshold (step S40), so as to determine whether the testing strip 1 is abnormal or not. To be noted, in this embodiment, the threshold used for the comparison in this stage (i.e. the trigger current TC generated by injecting the target sample to the testing strip 1) is defined as the first threshold marked as TH1, which is a current value here for example. In logic design, the procedure of the step S40 can be designed as determining whether the trigger current TC is larger than or equal to the first threshold TH1, and if the result is "no" (i.e. the trigger current TC is less than the first threshold TH1), a step of displaying a message for abnormality is executed (step S42). If the result is, on the other hand, "yes" (i.e. the trigger current TC is larger than or equal to the first threshold TH1), a step of entering into a reaction stage marked as RS (step S44) is executed.

As shown in FIG. 2A, the measuring module 2 of this embodiment further includes a process unit 23, which can receive the current value, i.e. the value of the trigger current TC, detected by the detecting unit 22, and execute the step S40 for the comparison and the subsequent operation of displaying the message for abnormality (step S42), or entering into the reaction stage RS (step S44). Furthermore, if the process unit 23 determines that the trigger current TC is less than the first threshold TH1, it represents that the testing strip 1 is probably abnormal, and therefore, the process unit 23 can directly transmit a message for abnormality to a display unit 24, so that the display unit 24 displays a message for abnormality (step S42). In other words, the message for abnormality is directly displayed while the subsequent reaction stage RS is not executed, so that scenario of displaying the abnormal (erroneous) reading and the misjudgment of the user can be avoided.

On the contrary, if the process unit 23 determines the trigger current TC is larger than or equal to the first threshold TH1, it represents the testing strip 1 is normal so that the step of entering into the reaction stage RS (step S44) can be executed. The reaction stage RS of this embodiment indicates the stage when the target sample generates the electrochemical reaction, i.e. the stage when the blood glucose of the whole blood (under-test object) and the reagent generate the electrochemical reaction (i.e. the reaction stage RS as shown in FIG. 3). Practically, in the reaction stage RS, the process unit 23 can control the power supply unit 21 to further supply a first driving voltage as the energy source required for the electrochemical reaction. The first driving voltage of this embodiment can be equal to the trigger voltage, i.e. 0.3V, and can be supplied to the testing strip 1 by the power supply unit 21 in the step S44. Likewise, after the electrochemical reaction generated between the target sample and the reagent, the corresponding reading current RC will be generated, which is called the first reading current RC1 here. In this embodiment, the process unit 23 executes a conversion formula to convert the first reading current RC1 into the corresponding reading (value), which can be blood glucose data, heavy metal concentration data, or drug residue data for example according to the applied field of the testing strip 1. Herein for example, the above mentioned reading is the blood glucose data of the whole blood (target sample). To be noted, the blood glucose data (the reading) derived from the computation of the detected first reading current RC1 is the original blood glucose data, i.e. un-calibrated blood glucose (level) data.

Figure 5:
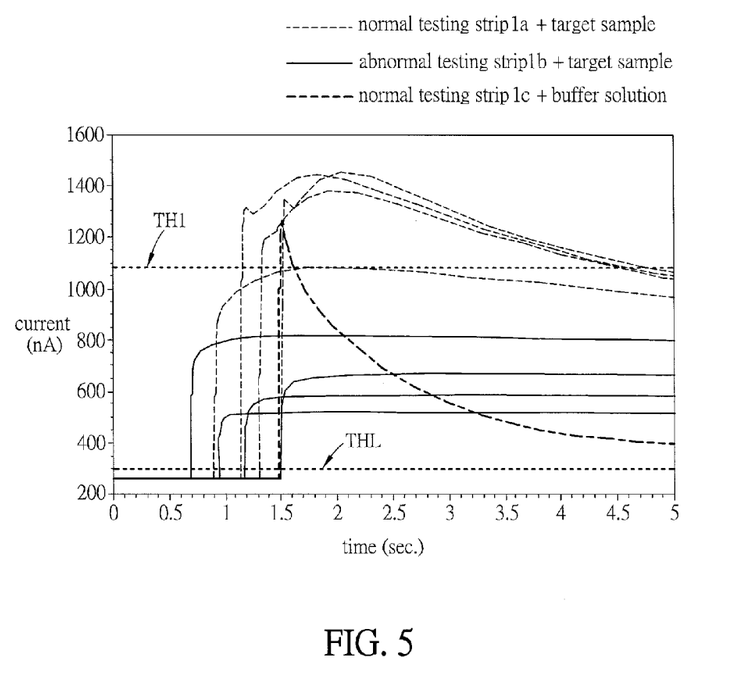
FIG. 5 is a schematic diagram of the time-current variation of the trigger current measured by the measuring module in FIG. 2A.

Besides, this embodiment further detects the first reading currents of the normal testing strip 1a and abnormal testing strip 1b so as to verify the method. FIG. 5 is a schematic diagram of the time-current variation of the trigger current TC measured by the measuring module in FIG. 2A. To be noted, in FIG. 5, the normal testing strip 1a and the abnormal testing strip 1b which both contain the target sample of the whole blood are regarded as the experimental group while the normal testing strip 1c plus the buffer solution as the target sample is regarded as the control group. Besides, FIG. 5 shows the trigger stage TS in FIG. 3. Moreover, in this experiment, the resistance of the normal testing strips 1a, and 1c is set as 20.8K Ohm, while the resistance of the abnormal testing strip 1b is set as 102K Ohm. In FIG. 5, the first threshold marked as TH1 can be in a range between 800 and 1200 nA favorably, the trigger current TC of the abnormal testing strip 1b has a descending tendency, and the first reading current RC1 at its rear side also has a descending and abnormal tendency. When the trigger current TC is larger than or equal to 800 nA, the normal testing strip 1a shows upwardly, so the first threshold TH1 can be set as 800 nA or a higher value. Further, in order to avoid the misjudging situation, the first threshold can be even set as any number between 800 and 1200 nA, such as a level about 1100 nA as the dashed line shown at upper part of FIG. 5 in this embodiment.

Figure 6:
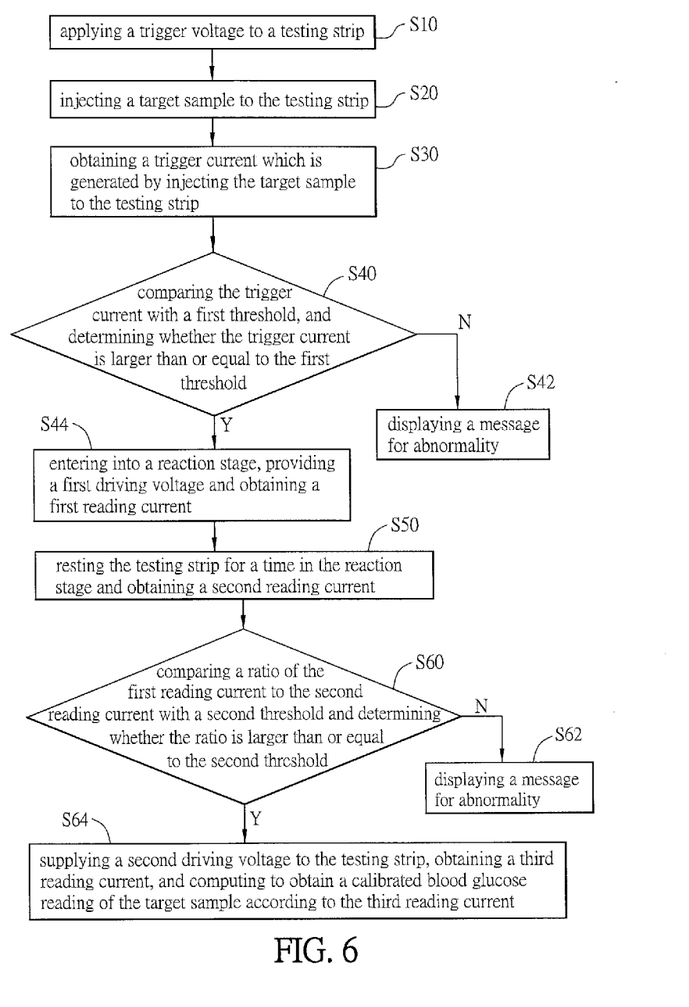
FIG. 6 is a schematic flowchart of the examination method for detecting abnormal electrochemical testing strip of another embodiment of the invention.

The reading corresponding to the detected first reading current RC1 in the above-mentioned embodiment is the original blood glucose value instead of the calibrated blood glucose value. Because some factors, such as the interfering object (e.g. impurities) excluding the under-test object (blood glucose), existing in the target sample will affect the measuring result and add error into the measured reading, some process needs to be implemented for the above interfering factors so as to obtain more correct blood glucose concentration. Therefore, in other embodiments, there further can be the subsequent calibration and the corresponding step to determine whether the testing strip is abnormal or not FIG. 6 is a schematic flowchart of the method for detecting abnormal electrochemical testing strip of another embodiment of the invention. As shown in FIGS. 3 and 6, the steps S10~S42 can be comprehended by referring to the above embodiments and are thus not described here for conciseness, and this embodiment further includes the step of: resting the testing strip 1 for a time Tr (i.e. rest time interval) in the reaction stage RS (step S50) following the above step S44 of obtaining the first reading current RC1. Meanwhile, since the electrochemical reaction tends to become gentle, the first reading current RC1 has a descending tendency and finally comes to a substantially fixed value. Accordingly, if the descending tendency of the reading appears abnormal (i.e. too fast or too slow a curve), it may indicate the abnormal testing strip 1, so this phenomenon can be regarded as another basis for determining whether the testing strip 1 is abnormal or not.

The detailed operation is illustrated as below. A reading current obtained after a period or interval of the rest Tr can be defined as the second reading current marked as RC2 (step S50). The rest time Tr is about a short interval of one second to two seconds, which can be adjusted according to the variety of under-test object, reagent, supplied reaction driving voltage or examination environment (such as temperature or humidity), as comprehended by those skilled in the art. Another judgment mechanism can be used at this stage, including the steps of: computing a ratio of the above-mentioned measured first reading current RC1 to the second reading current RC2 (R=RC1/RC2), and then comparing the ratio R with a second threshold marked as TH2 (referring to FIG. 7) and determining whether the ratio R is larger than or equal to the second threshold TH2 (step S60); displaying a message for abnormality when the ratio R is less than the second threshold TH2 (step S62), or computing to obtain a calibrated blood glucose reading of the target sample when the ratio R is larger than or equal to the second threshold TH2 (step S64). The details related to the above-mentioned second threshold TH2 and step S64 will be illustrated later.

As shown in FIGS. 2A and 6, in the step S64, a second driving voltage is supplied to the testing strip 1 by the power supply unit 21 in the reaction stage RS so as to obtain another corresponding reading current, which is called the third reading current herein. The second driving voltage is greater than the first driving voltage and/or the trigger voltage (0.3V), and is in a range between 1 and 4V favorably. After the second driving voltage is applied, the electrochemical reaction of the target sample and reagent will lead to the corresponding third reading current. When the process unit 23 receives the third reading current, the hematocrit index (HCT index, abbreviated to HCT hereinafter) corresponding to the target sample can be derived from a formula and the obtained third reading current, and the calibrated blood glucose value can be acquired through the further computation.

By going back to the above mentioned step S60, the process unit 23 compares the ratio R of the first reading current RC1 to the second reading current RC2 with the second threshold TH2, and determines whether the ratio R is greater than or equal to the second threshold TH2. If the result is "no", it represents the ratio R is less than the second threshold TH2. Since this may be caused by the abnormal testing strip 1, the process unit 23 can directly transmit a message for abnormality to the display unit 24 so that the display unit 24 can display a message for abnormality (step S62). In other words, the subsequent computation for the calibrated blood glucose value needn't be executed, and besides, directly displaying the message for abnormality can avoid displaying the abnormal (erroneous) reading. Likewise, if the determination of the process unit 23 is "yes", it represents the ratio R is greater than or equal to the second threshold TH2, and thus the testing strip 1 is normal, so that the subsequent computation can be executed to compute to obtain a blood glucose reading of the target sample (step S64). That is, the calibrated blood glucose value can be obtained and displayed by the display unit 24 for the user's reference.

Figure 7:
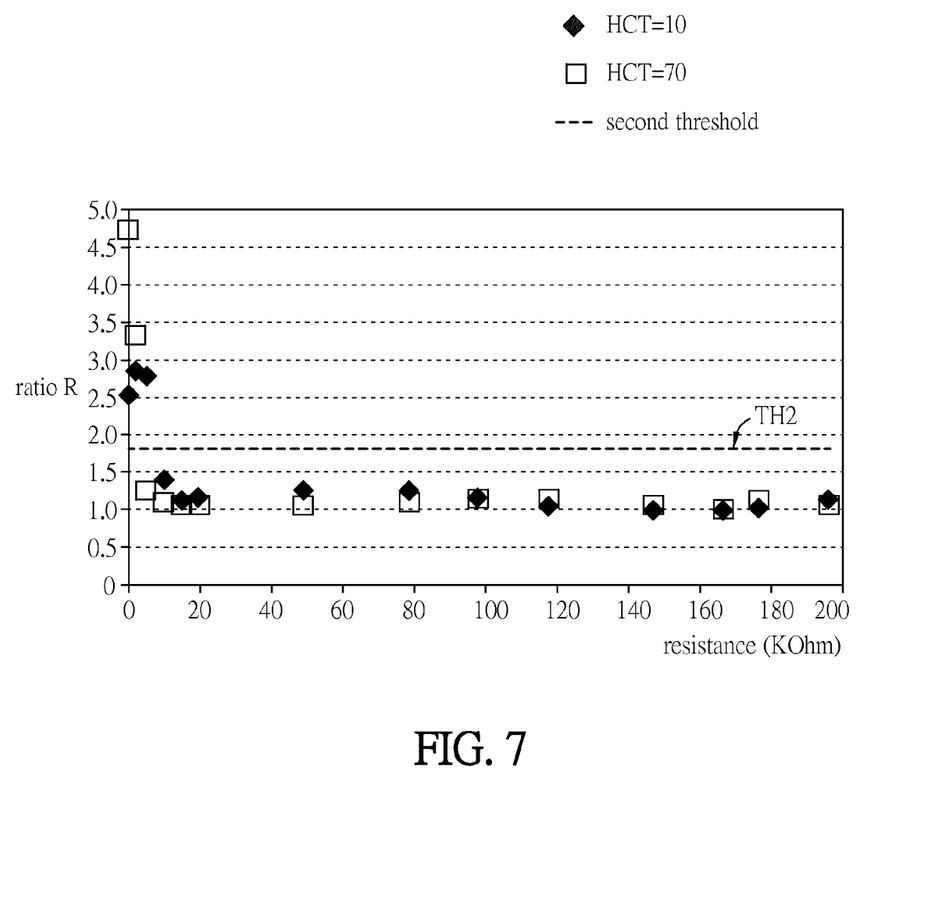
FIG. 7 is a schematic diagram of the ratio of the first reading current to the second reading current measured by the measuring module in FIG. 2A.

FIG. 7 is a schematic diagram of the ratio of the first reading current to the second reading current measured by the measuring module in FIG. 2A. As shown in FIGS. 7 and 2A, to be noted, the X axis in FIG. 7 represents the resistance value of the testing strip 1, and the larger resistance value corresponds to the more abnormal situation, wherein unit of the X axis here is K Ohm. The resistance value of the testing strip is generally in a range between 1 and 2 KOhm, and FIG. 7 can show the variation tendency (in Y axis) of the corresponding ratio R of the first reading current RC1 to the second reading current RC2 when the resistance value of the testing strip 1 abnormally ascends. Besides, in FIG. 7, two target samples with HCT of 10 and 70 are taken in the experiment respectively. In FIG. 7, it can be noted that the increased resistance value leads to the descending tendency of the ratio R for both of the target samples with HCT of 10 and 70, and this characteristic conforms to the above-mentioned dynamic balance, too. Moreover, in FIG. 7, it can be shown, favorably, the second threshold TH2 is a pure number, which can be between 1.5 and 2.5, and favorably about 1.8 (times) as the dashed line shown at middle part of FIG. 7 in this embodiment.

Figure 8:
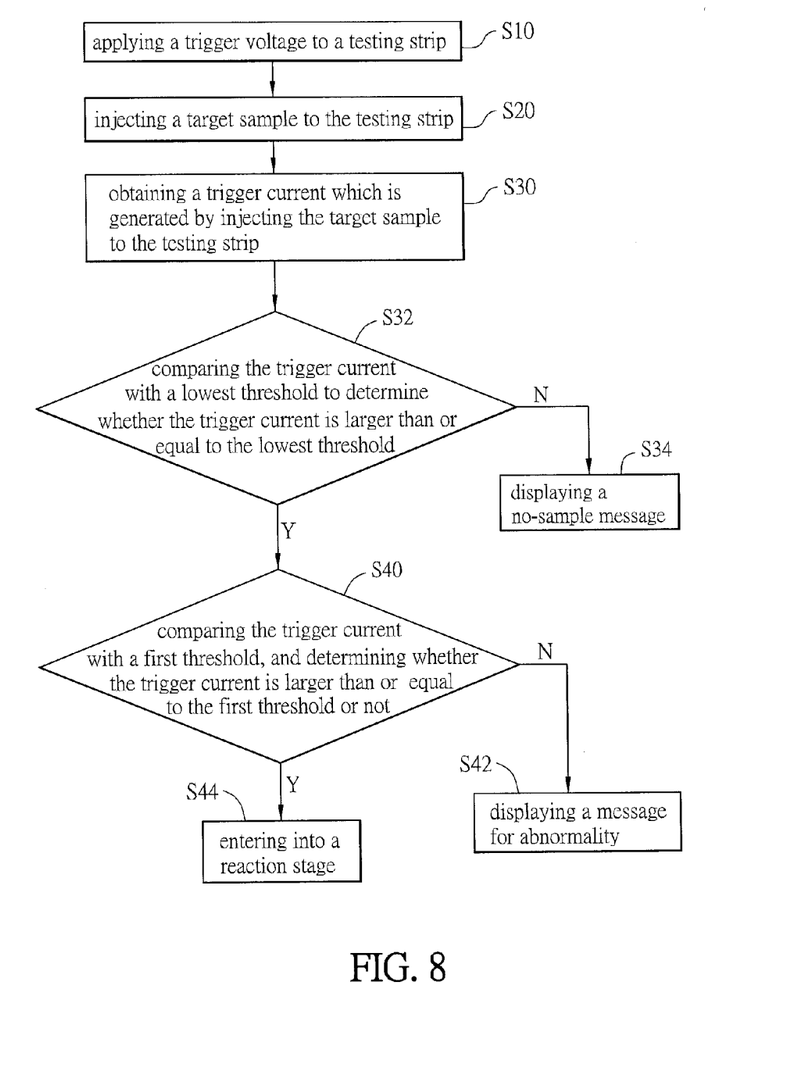
FIG. 8 is a schematic flowchart of an examination method for detecting abnormal electrochemical testing strip of yet another embodiment of the invention.

In other embodiments, before the step S40 of comparing the trigger current TC with the first threshold TH1, there can be further a confirmation step to confirm if the target sample is indeed injected to the testing strip 1. FIG. 8 is a schematic flowchart of an examination method for detecting abnormal electrochemical testing strip of yet another embodiment of the invention, and in this method, before the step S40, further includes the steps of: comparing the trigger current TC with a lowest threshold marked as THL to determine whether the trigger current TC is larger than or equal to the lowest threshold THL (step S32); displaying a "no-sample" message when the trigger current TC is less than the lowest threshold THL (step S34) or entering into the comparison step with the first threshold TH1 (i.e. the above-mentioned step S40) when the trigger current is larger than or equal to the lowest threshold THL. Because the step S32 is used to determine whether the target sample is indeed injected into the testing strip 1 or not, the lowest threshold THL can be set or defined to be a lower value (compared to the first threshold TH1). For example, the lowest threshold THL can be less than the first threshold TH1, and favorably as shown in FIG. 5, the lowest threshold THL can be set in a range between 300 and 600 nA, and for example the lowest threshold THL can be set at about 300 nA as the dashed line shown at bottom part of FIG. 5 in this embodiment.

As shown in FIGS. 2A and 3, likewise, the process unit 23 receives the trigger current TC and compares it with the lowest threshold THL to determine whether the trigger current TC is larger than or equal to the lowest threshold THL or not. If the determination result is "no", it represents the trigger current TC is less than the lowest threshold THL, and this may be because the target sample is not yet correctly or completely injected into the testing strip 1, i.e. underfilled. Accordingly, the process unit 23 can directly transmit a "no-sample" message to the display unit 24, so that the display unit 24 displays a "no-sample" message (step S34) to warn the user to inject the target sample correctly or completely for the measuring. On the other hand, if the determination of the process unit 23 is result "yes", it represents the trigger current TC is larger than or equal to the lowest threshold THL. Accordingly, the testing strip 1 indeed contains the target sample to a proper amount suitable for testing, and then the target sample can be compared with the (relative) higher first threshold TH1 (step S40). Since the subsequent steps can be comprehended by referring to the steps S42 and S44 in FIG. 1 or the steps S40~S64 in FIG. 6 and their corresponding illustration, the related description is omitted here for conciseness.

Summarily, in the examination method for detecting abnormal electrochemical testing strip of this invention, the dynamic balance property existing between the trigger current TC and the reading current RC which are generated due to the electrochemical reaction of the target sample is used, and thereby the trigger current TC and a threshold (i.e. the first threshold TH1) are compared with each other to determine whether the testing strip 1 is abnormal or not. If it is determined that the trigger current TC is less than the first threshold TH1, it represents the testing strip 1 is probably abnormal so as to lead to a too small value, and therefore a message for abnormality can be displayed in time. Therefore, the message for abnormality is directly displayed to inform the user while the subsequent reaction stage RS (i.e. the stage when the target sample and the reagent generate the electrochemical reaction) needn't be executed, so that displaying the abnormal (erroneous) reading and the misjudgment of the user can be avoided.

Furthermore, on the other hand, if the trigger current TC is larger than or equal to the first threshold TH1 and the reaction stage RS is thus executed, a confirmation mechanism is further designed for the reaction stage RS in this invention. That is, the ratio R of the first reading current RC1 to the second reading current RC2 measured in the reaction stage RS is compared with the second threshold TH2, and if it is determined that the Ratio R is less than the second threshold TH2, it represents the testing strip 1 is probably abnormal so as to lead to a too small value, and therefore a message for abnormality can be displayed in time. Accordingly, one more chances for the debugging can be provided, and the usage can be more enhanced in reliability. Moreover, this invention also supplies a larger driving voltage (i.e. the second driving voltage larger than the trigger voltage and the first driving voltage) for the target sample with different HCT concentration in the reaction stage RS to obtain the corresponding reading current TC (here defined as the third reading current in this embodiment as mentioned above). In general, the third reading current is used for the conversion to calibrate the HCT index to compute the correct blood glucose value so as to determine whether the testing strip 1 is abnormal or not.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An examination method for detecting abnormal electrochemical testing strip, comprising steps of:
   applying a trigger voltage to a testing strip;
   injecting a target sample to the testing strip;
   obtaining a trigger current which is generated by injecting the target sample to the testing strip;
   comparing the trigger current with a lowest threshold to determine whether the trigger current is larger than or equal to the lowest threshold;
   displaying a no-sample message when the trigger current is less than the lowest threshold, or
   entering into the step of comparing the trigger current with a first threshold and determining whether the trigger current is larger than or equal to the first threshold when the trigger current is larger than or equal to the lowest threshold; and
   displaying a message for abnormality when the trigger current is less than the first threshold in the step of comparing the trigger current with the first threshold and determining whether the trigger current is larger than or equal to the first threshold.

2. The examination method as recited in claim 1, wherein the step of determining whether the trigger current is larger than or equal to the first threshold enters into a reaction stage when the trigger current is larger than or equal to the first threshold.

3. The examination method as recited in claim 2, wherein the reaction stage indicates the stage when the target sample generates the electrochemical reaction, and a first driving voltage is supplied in the reaction stage to obtain a first reading current.

4. The examination method as recited in claim 3, further comprising steps of:
   supplying the first driving voltage to the testing strip and then resting the testing strip for a time interval to obtain a second reading current;
   comparing the ratio of the first reading current to the second reading current with a second threshold to determine whether the ratio is larger than or equal to the second threshold; and
   when the ratio is less than the second threshold, displaying the message for abnormality.

5. The examination method as recited in claim 4, further comprising a step of:
   when the ratio is larger than or equal to the second threshold, supplying a second driving voltage to the testing strip to obtain a third reading current after the testing strip is rested for the time interval.

6. The examination method as recited in claim 5, further comprising a step of:
   calibrating a blood glucose reading of the target sample according to the third reading current.

7. The examination method as recited in claim 4, wherein the time interval for the resting step is between 1 second and 2 seconds.

8. The examination method as recited in claim 4, wherein the second threshold is between 1.5 and 2.5 times.

9. The examination method as recited in claim 1, wherein the first threshold is between 800 and 1200 nA.

10. The examination method as recited in claim 1, wherein the lowest threshold is less than the first threshold.

11. The examination method as recited in claim 1, wherein the lowest threshold is between 300 and 600 nA.

12. An examination method for detecting abnormal electrochemical testing strip, comprising steps of:
   applying a trigger voltage to a testing strip;
   injecting a target sample to the testing strip;
   obtaining a trigger current which is generated by injecting the target sample to the testing strip;
   comparing the trigger current with a first threshold, and determining whether the trigger current is larger than or equal to the first threshold;
   displaying a message for abnormality when the trigger current is less than the first threshold, or
   entering into a reaction stage when the trigger current is larger than or equal to the first threshold;
   supplying a first driving voltage to the testing strip in the reaction stage to obtain a first reading current;
   resting the testing strip for a time interval to obtain a second reading current;
   comparing the ratio of the first reading current to the second reading current with a second threshold to determine whether the ratio is larger than or equal to the second threshold; and displaying the message for abnormality when the ratio is less than the second threshold.

13. The examination method as recited in claim 12, wherein after the step of supplying the first driving voltage to the testing strip in the reaction stage, further comprises a step of:
supplying a second driving voltage to the testing strip to obtain a third reading current when the ratio is larger than or equal to the second threshold.

14. The examination method as recited in claim 13, further comprising a step of:
calibrating a blood glucose reading of the target sample according to the third reading current.

15. The examination method as recited in claim 12, wherein the time interval for the resting step is between 1 second and 2 seconds.

16. The examination method as recited in claim 12, wherein the first threshold is between 800 and 1200 nA.

17. The examination method as recited in claim 12, wherein the second threshold is between 1.5 and 2.5 times.

18. The examination method as recited in claim 12, wherein before the step of comparing the trigger current with the first threshold, further comprises steps of:
comparing the trigger current with a lowest threshold to determine whether the trigger current is larger than or equal to the lowest threshold; and displaying a no-sample message when the trigger current is less than the lowest threshold, or entering into the step of comparing the trigger current with the first threshold when the trigger current is larger than or equal to the lowest threshold.

19. The examination method as recited in claim 18, wherein the lowest threshold is between 300 and 600 nA.

\* \* \* \* \*